United States Patent [19]
Collyer

[11] Patent Number: 5,496,010
[45] Date of Patent: Mar. 5, 1996

[54] CLOSURE MEANS

[75] Inventor: Graham J. Collyer, Via Hyde, United Kingdom

[73] Assignee: Simpla Plastics Limited, Cardiff, Wales

[21] Appl. No.: 310,809

[22] Filed: Sep. 22, 1994

Related U.S. Application Data

[63] Continuation of Ser. No. 174,421, Dec. 28, 1993, abandoned, which is a continuation of Ser. No. 836,008, filed PCT/GB90/01356, Sep. 3, 1990, abandoned.

[30] Foreign Application Priority Data

Sep. 2, 1989 [GB] United Kingdom .................. 8919872

[51] Int. Cl.$^6$ ............................................ F16K 5/00
[52] U.S. Cl. ............................ 251/78; 251/231; 251/248; 251/309; 604/323; 604/335
[58] Field of Search ............................ 251/78, 231, 248, 251/250.5, 309; 604/32, 248, 323, 326, 335

[56] References Cited

U.S. PATENT DOCUMENTS

| | | | |
|---|---|---|---|
| 746,762 | 12/1903 | Totham | 251/260 |
| 754,889 | 3/1904 | Peck | 251/260 |
| 760,706 | 5/1904 | Schroeder | 251/260 |
| 2,544,161 | 3/1951 | Hinrichs | 251/260 |
| 3,687,414 | 8/1972 | Petty | 251/77 |
| 4,540,156 | 9/1985 | Cross | 251/309 |
| 4,966,551 | 10/1990 | Betush | 604/32 X |

FOREIGN PATENT DOCUMENTS

| | | | |
|---|---|---|---|
| 620068 | 5/1961 | Canada | 251/309 |
| 3528656 | 7/1986 | Germany | 251/309 |
| 708047 | 4/1954 | United Kingdom | 251/248 |
| 2166222 | 4/1986 | United Kingdom | 251/309 |

*Primary Examiner*—Gerald A. Michalsky
*Attorney, Agent, or Firm*—Synnestvedt & Lechner

[57] ABSTRACT

A urine drainage tap is provided which includes an elongated passage having a barrel disposed therein and a control member located in the barrel which is moveable in relation to the barrel for defining an open and closed position. The lever arm is connected to the control member to permit movement of the control member. In an important aspect of this invention, the lever arm is moveable so as to extend along the passage in substantially opposite longitudinal directions relative to the passage when the control member is in the open and closed positions so as to avoid the tendency for the patient to inadvertently open or close the control member by leaning on the lever arm.

3 Claims, 6 Drawing Sheets

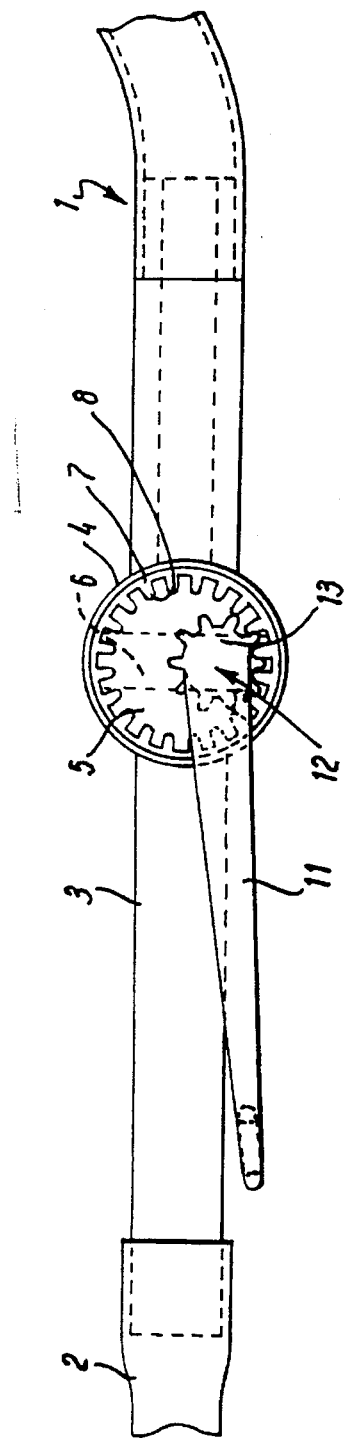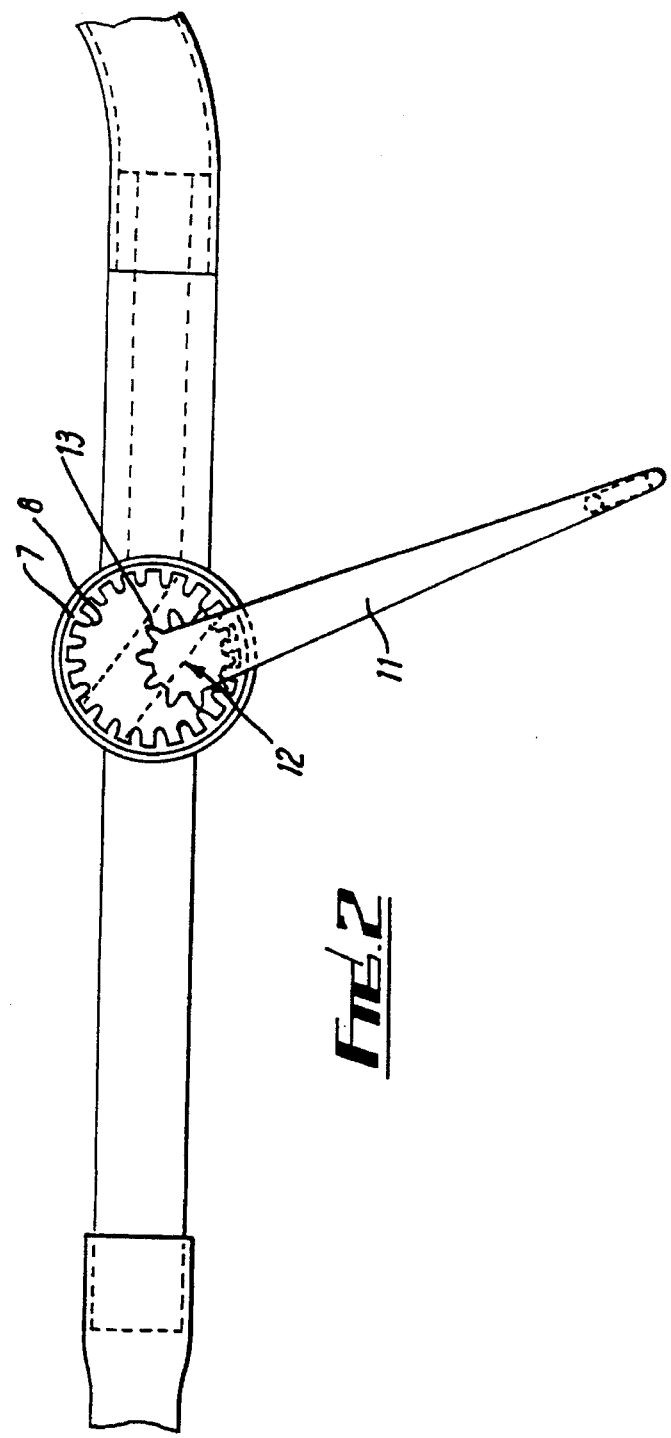

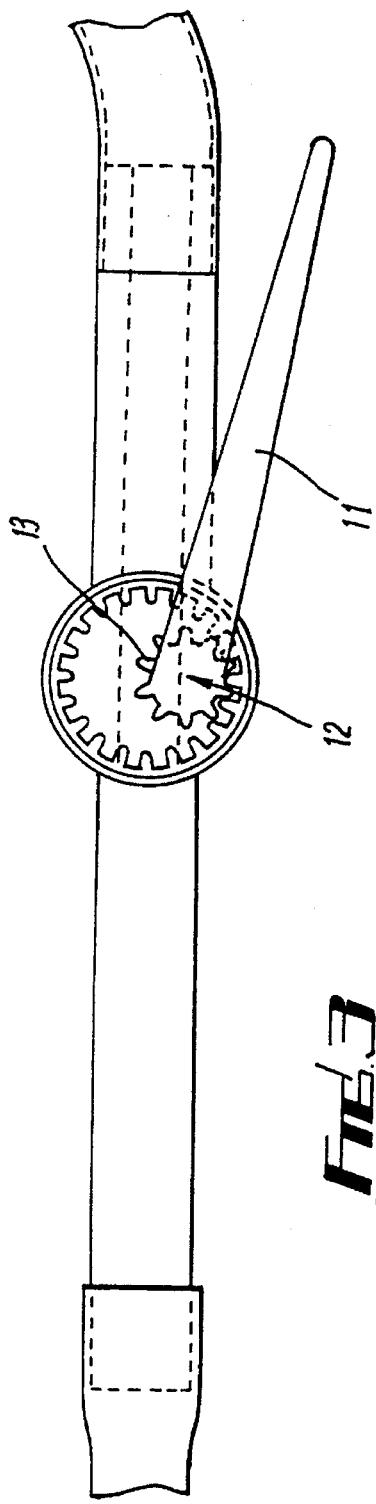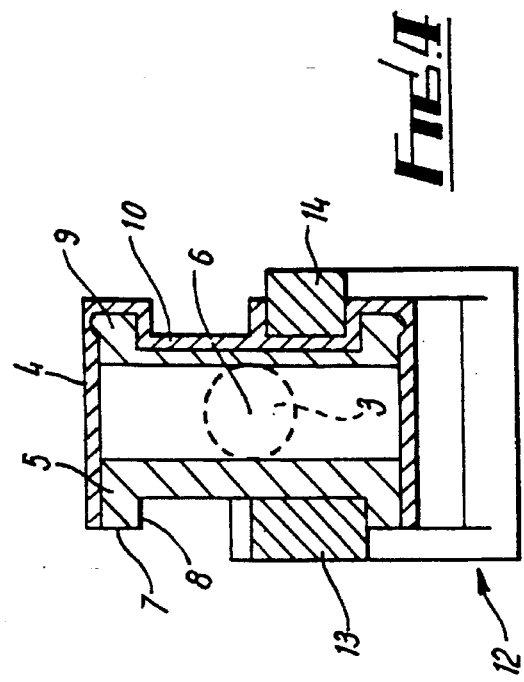

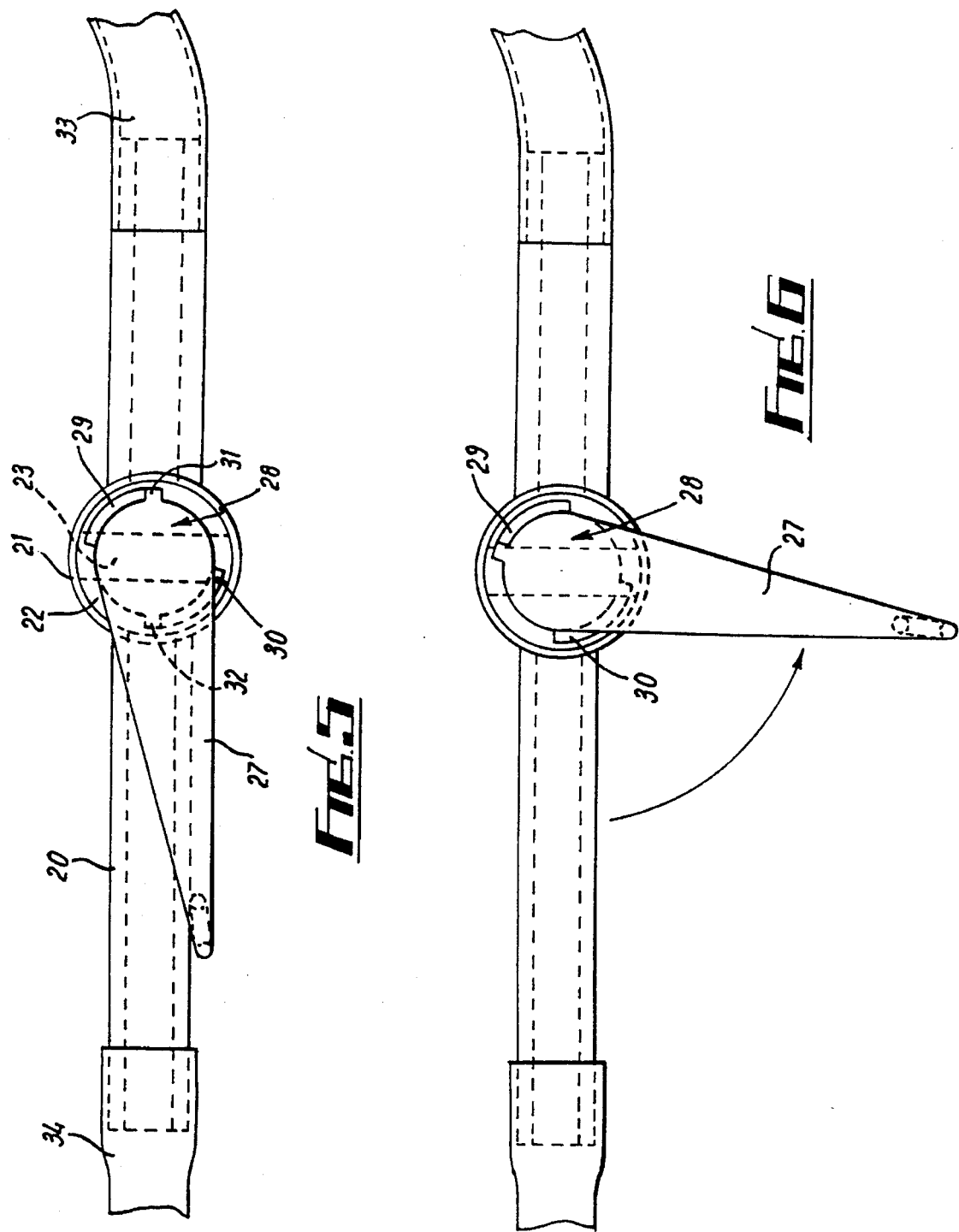

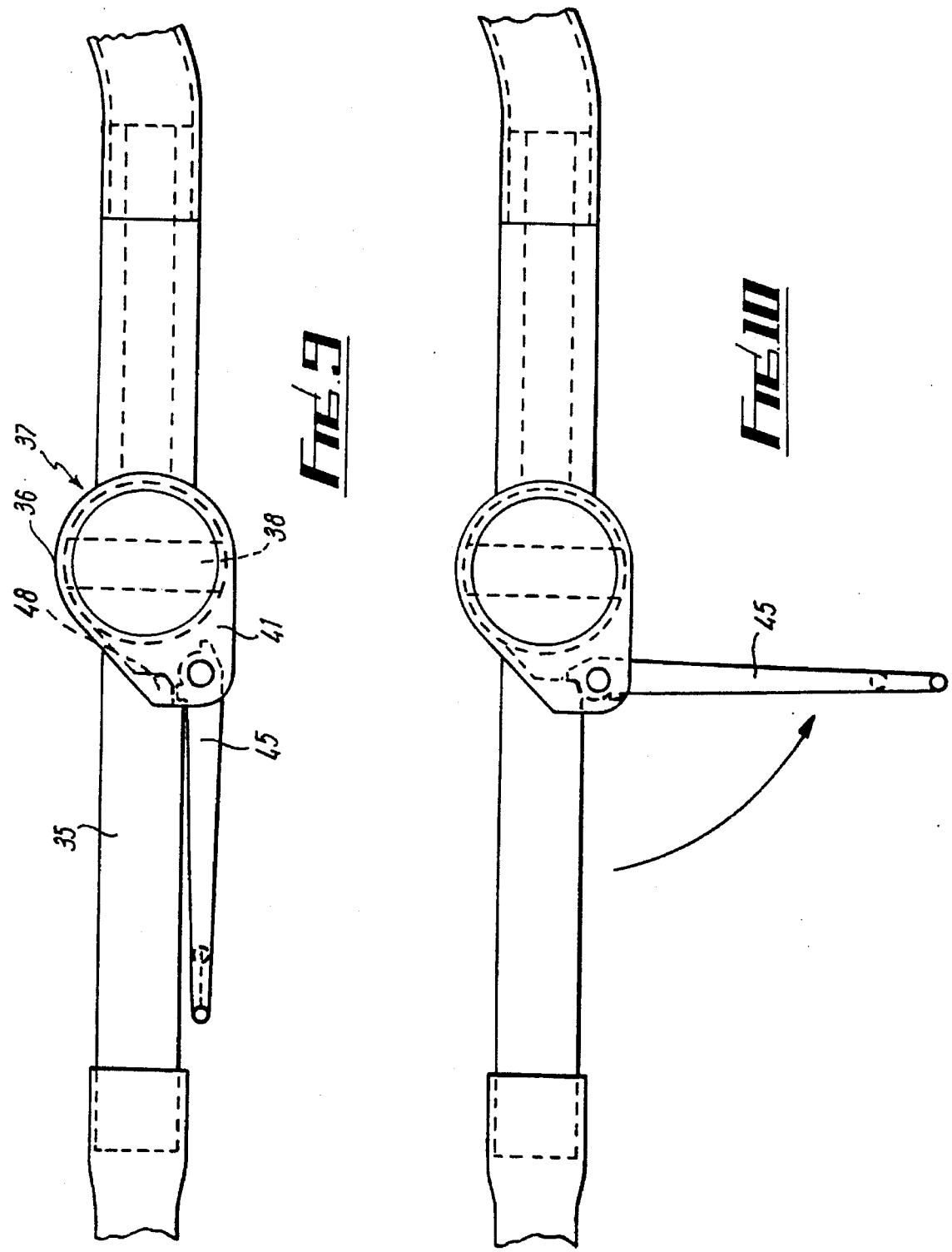

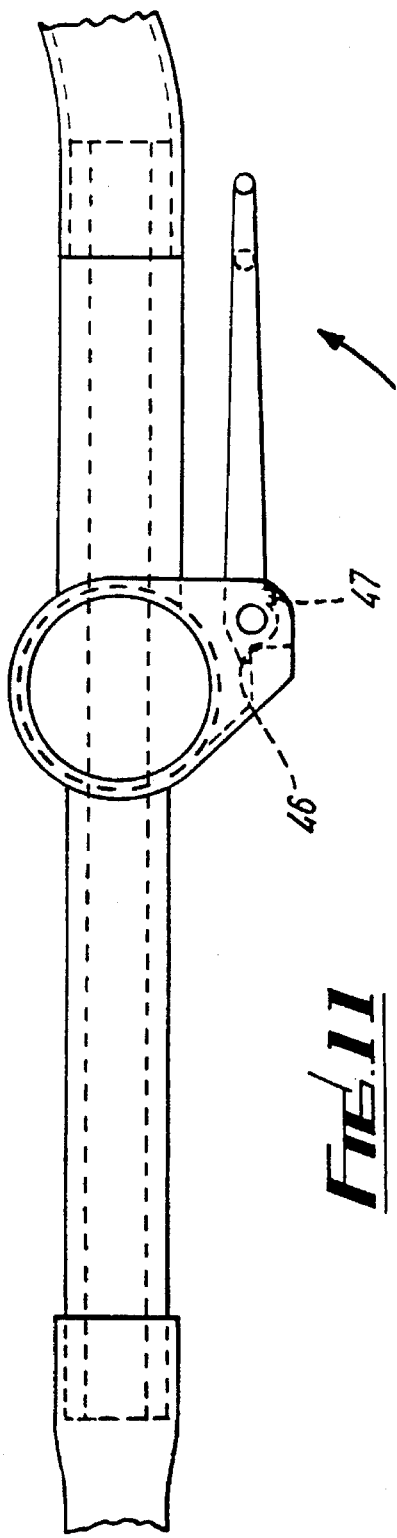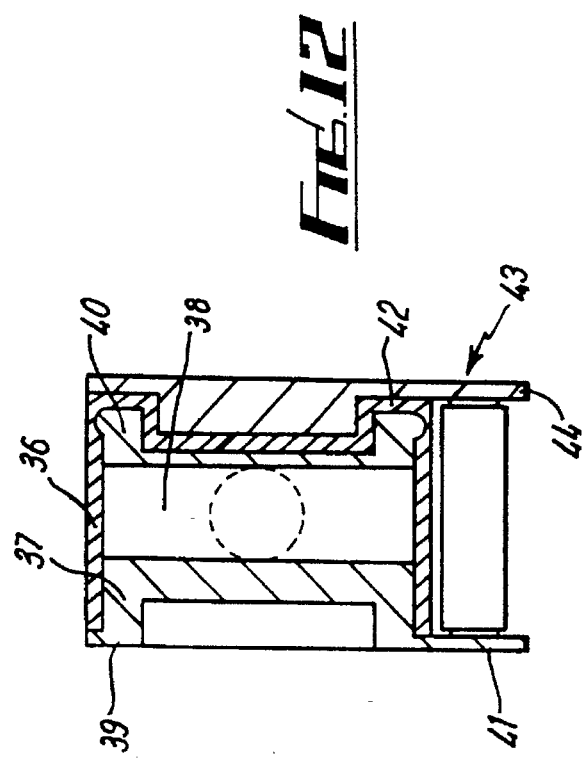

5,496,010

CLOSURE MEANS

This is a continuation of application Ser. No. 08/174,421 filed on Dec. 28, 1993, now abandoned, which is a continuation of application Ser. No. 07/836,008, filed as PCT/GB90/01356, Sep. 3, 1990, now abandoned.

TECHNICAL FIELD

This invention relates to a closure means in the form of a tap particularly although not exclusively for use with a urine collection bag.

BACKGROUND ART

With urine bags that are attached to the upper or lower leg for daytime use, it is usual to provide a shut off tap where the bag is to be connected to a bedside bottle or bag for overnight use. The tap is customarily connected to the bag in a length of tubing close to the person's body and this can give rise to problems in the usual case where the tap has a projecting lever arm which is movable between a closed position generally parallel to the length of tubing and an open position generally at right angles thereto. In the open position the projecting lever arm may press into the person's body and may be inadvertently moved to the closed position for example when the person turns over in his sleep.

An object of the present invention is to provide a tap having a lever arm which need not project unduly in either open or closed positions thereof.

DISCLOSURE OF THE INVENTION

According to the invention therefore there is provided a tap comprising an elongate passage incorporating a barrel, a control member movable between open and closed positions within the barrel, and a lever arm connected to the control member to effect movement thereof, characterized in that the lever arm is movable so as to extend in substantially opposite longitudinal directions relative to said passage in each said position of the control member.

With this arrangement conveniently the tap is operated by a lever arm but there is no need for the arm to project unduly from the elongate passage in with the open or closed positions of the tap.

Preferably the lever arm is connected to the control member via an intermediate device which is arranged such that the movement of the lever arm between the opposite longitudinal positions thereof corresponds to a much smaller degree of angular movement (preferably about 90°) of the control member.

Thus in one embodiment the intermediate device comprises a gear arrangement which may comprise meshing toothed gears which may give substantially 2:1 gearing or any other suitable ratio. The lever arm may have a toothed wheel which meshes with the inner toothed periphery of a ring on the control member.

In a further embodiment the intermediate device comprises a lost motion linkage whereby the control member is drivably linked with the lever arm over only part (e.g. approximately half) of the path of movement thereof. Thus, the lever arm may be pivotally connected to the control member with an abutment on the lever arm which is engageable with an abutment on the control member to effect drivable interconnection therebetween during said part of said path of movement.

BRIEF DESCRIPTION OF THE DRAWINGS

The invention will now be described further by way of example only and with reference to the accompanying drawings in which:

FIGS. 1 to 3 are side views in different operating positions of one form of a tap according to the invention;

FIG. 4 is a sectional view through the tap of FIG. 1;

FIGS. 5 to 8 are views corresponding to FIGS. 1 to 4 of an alternative embodiment; and FIGS. 9 to 12 are views corresponding to FIGS. 1 to 4 of a yet further embodiment.

BEST MODES FOR CARRYING OUT THE INVENTION

Figure 7:
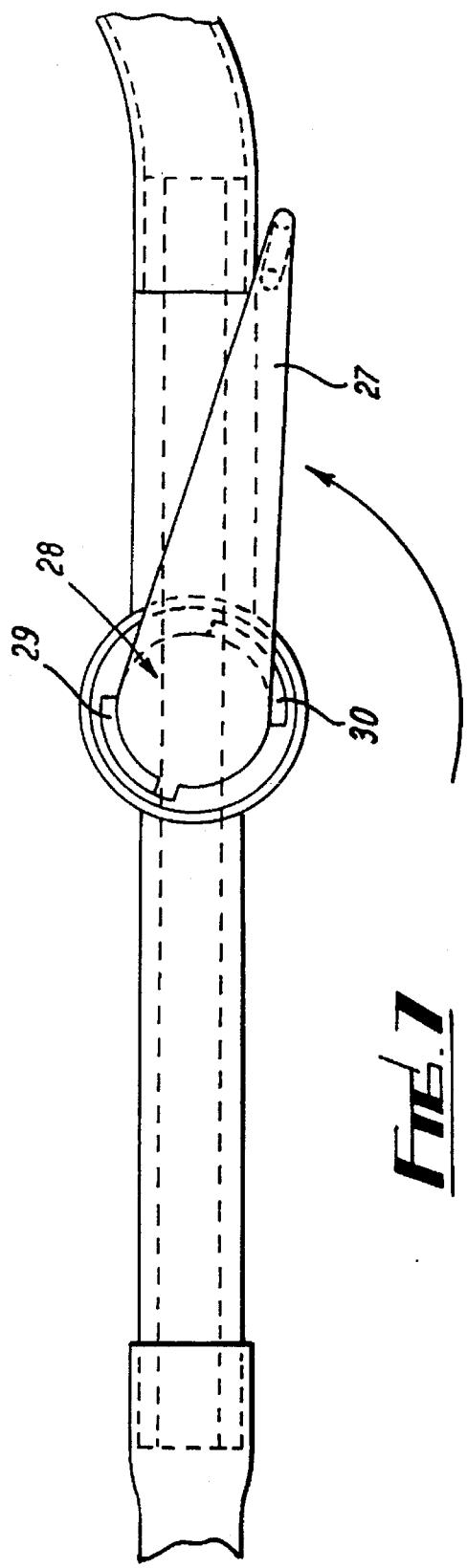

Referring to FIGS. 1 to 4, a tap is interconnected between a urine collection bag 1, for example of the kind commonly referred to as a 'Leg Bag' and a tube 2 joined to an overnight reservoir bottle or bag. The tap comprises a length of tubing 3 with a transverse cylindrical barrel 4 containing a close fitting cylindrical control member 5 with a through diametrically extending bore 6. The barrel 4 has opposite side openings in communication with the tubing 3.

At one end, the control member 5 has an outwardly directed peripheral ring-shaped extension 7 with equally spaced teeth 8 on its inner periphery. At the other end the member 5 has a ring-shaped extension 9 which engages a shaped end part 10 of the barrel.

The tap further comprises a lever arm 11 having a forked structure 12 at one end which straddles the barrel 4. A small toothed wheel 13 is formed integrally with one part of the forked structure and is located within so as to mesh with the toothed ring 7. The opposed part 14 of the forked structure 12 seats pivotally in the shaped end part 10 of the barrel 4.

The lever arm 11 can be pivoted, by rotation of the wheel 13 in mesh with the ring 7, between one limit position in which the lever arm 11 extends substantially longitudinally of the tubing 3 pointing towards the bag or bottle tube 2 and an opposite limit position in which the lever arm 11 extends substantially longitudinally of the tubing 3 pointing towards the bag 1.

As the lever arm 11 pivots between these limit positions the control member 5 rotates within the barrel 4 from a closed position at which the bore 6 is at right angles to the tubing 3 and thereby prevents flow therealong, and an open position at which the bore 6 is aligned with the tubing 3. In an intermediate position the tap is partially open.

With this arrangement it will be seen that the lever arm 11 lies alongside the tubing 3 in each of the open and closed positions of the tap. There is therefore no need for the arm 11 to project inconveniently away from the tubing 3 in any normal operating position thereof.

Thus, the known advantages of the projecting lever arm/barrel type tap, i.e. ease of operation, simplicity, reliability, convenient to install and dismantle for cleaning, can be utilized, without the usual disadvantage of having a lever arm which projects appreciably in use.

Figure 8:
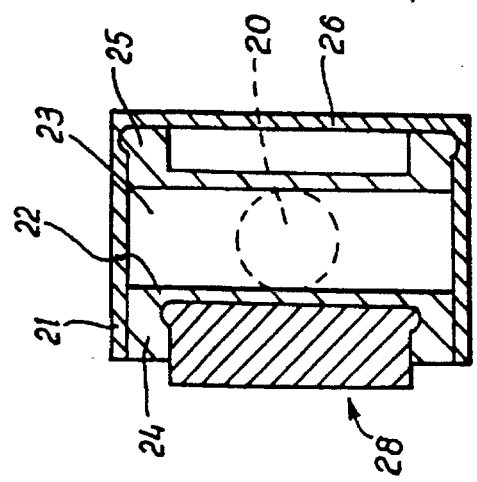

With reference to the embodiment of FIGS. 5–8 this shows a tap which has tubing 20, and a barrel 21 containing a rotatable close fitting control member 22 with a diametric bore 23 in like manner to FIGS. 1–4.

The control member 22 also has peripheral ring-shaped extensions 24, 25 one of which (25) is seated against end part 26 of the barrel 21. The tap has an arm 27 which has a single side part 28 at one end which is connected to one of the ends of the control member 22.

At said end of the member 22, the ring-shaped extension 24 has two, opposed part circular slots 29, 30 engaged by opposed projections 31, 32 on an inner face of the side part 28 of the arm 27. The arm 27 is freely pivotally connected concentrically with the member 22. Thus, when the arm 27 is pivoted about the axis of the member 22 this will only result in rotation of the member 22 when the projections 31, 32 are at one or the other of the ends of the slots 29, 30 so as to engage such ends and thereby drivably interconnect the arm 27 and the member 22.

Accordingly, as with the first embodiment, movement of the arm 27 through approximately 180° causes movement of the member 22 through approximately 90°, this being a consequence of the lost motion introduced by the slots 29, 30 and projections 31, 32. The tap is in respective open and closed states when the lever arm 27 is disposed substantially longitudinally of the tubing 20 and pointing respectively towards the bag 33 and towards the bottle or bag tube 34.

With reference to FIGS. 9–12, these also show a tap with tubing 35 and a barrel 36 containing a close fitting control member 37 with a diametric bore 38, like the embodiment of FIGS. 1–4.

The control member 37 has ring-shaped extensions 39, 40 at its ends, one of which (39) has a radially outwardly directed extension part 41 at one side. The other ring-shaped extension 40 engages a shaped end part 42 of the barrel 36 and there is an end plate 43 which engages the outer side of this end part 42 and has an extension part 44 which is of like form to, and is aligned with, the other extension part 41.

A lever arm 45 is freely pivoted at one end between the confronting extension parts 41, 44 and there are two circumferentially spaced projecting lips 46, 47 at such end. The inner faces of the extension parts 41, 44 have abutments 48 thereon whereby the lever arm 45 can be pivoted to two limit positions in each of which a respective one of the lips 46, 47 engages the abutment 48 to drivably interconnect the arm 45 and the member 37.

Thus, as with the embodiment or FIGS. 5–8, movement or the arm 45 through approximately 180° causes the movement or the member 37 through approximately 90°, this being a consequence of the lost motion introduced by the pivotal interconnection between the arm 45 and the extension parts 41, 43.

It is or course to be understood that the invention is not intended to be restricted to the details or the above embodiments which are described by way or example only.

I claim:

1. A tap for interconnection between a urine collection bag and tubing means conjoined with urine reservoir means comprising:

(a) an elongate passage;

(b) a barrel, disposed within and substantially at a right angle to said passage;

(c) a control member disposed in said barrel and rotatable in relation thereto for defining therewith respective open and closed positions of said tap;

(d) a lever arm connected to the control member by an intermediate lost motion device whereby to effect rotatable movement of said control member on rotational movement of said lever arm; and (e) said lever arm extending in substantially opposite longitudinal directions relative to said elongate passage in said open and closed positions of said control member, said lever arm lying alongside and in close proximity to said elongate passage in each of said open and closed positions, wherein said lever arm is connected to and mounted for rotation with said control member by means of said lost motion device whereby rotation of the lever arm between said substantially opposite longitudinal directions effects a degree of angular movement of said control member which is substantially smaller than the angular movement of the lever arm.

2. A tap as defined in claim 1, wherein said intermediate lost motion device comprises a meshing toothed gear with a gear ratio of substantially 2:1.

3. A tap as defined in claim 2, wherein said lever arm has a toothed wheel which meshes with an inner toothed periphery of a ring on the control member.

* * * * *

UNITED STATES PATENT AND TRADEMARK OFFICE
CERTIFICATE OF CORRECTION

PATENT NO. : 5,496,010
DATED      : March 5, 1996
INVENTOR(S): Graham J. Collyer It is certified that error appears in the above-identified patent and that said Letters Patent is hereby corrected as shown below:

Column 3, line 41, each occurrence, change "or" to --of--.

Column 3, line 43, change "or" to --of--.

Column 4, line 4, change "or" to --of--.

Column 4, line 5, change "or" to --of--.

Column 4, line 6, change "or" to --of--.

Signed and Sealed this

Fifteenth Day of October, 1996

Attest:

BRUCE LEHMAN

Attesting Officer    Commissioner of Patents and Trademarks